(12) United States Patent
Rose et al.

(10) Patent No.: US 9,751,891 B2
(45) Date of Patent: Sep. 5, 2017

(54) METHOD FOR THE SYNTHESIS OF PRIMARY ISOHEXIDE AMINES

(71) Applicant: RHEINISCH-WESTFAELISCHE TECHNISCHE HOCHSCHLULE (RWTH) AACHEN, Aachen (DE)

(72) Inventors: Marcus Rose, Aachen (DE); Regina Palkovits, Aachen (DE); Rebecca Engel, Cardiff (GB); Alireza Haji Begli, Ramsen (DE); Christine Kroener, Obrigheim/Pfalz (DE)

(73) Assignee: RHEINISCH-WESTFÄLISCHE TECHNISCHE HOCHSCHLULE (RWTH) AACHEN, Aachen (DE)

(*) Notice: Subject to any disclaimer, the term of this patent is extended or adjusted under 35 U.S.C. 154(b) by 0 days.

(21) Appl. No.: 15/327,262

(22) PCT Filed: Jul. 18, 2014

(86) PCT No.: PCT/EP2014/065556
§ 371 (c)(1),
(2) Date: Jan. 18, 2017

(87) PCT Pub. No.: WO2016/008547
PCT Pub. Date: Jan. 21, 2016

(65) Prior Publication Data
US 2017/0174698 A1    Jun. 22, 2017

(51) Int. Cl.
C07D 493/04 (2006.01)
B01J 21/18 (2006.01)
B01J 23/46 (2006.01)
B01J 35/00 (2006.01)

(52) U.S. Cl.
CPC ............ *C07D 493/04* (2013.01); *B01J 21/18* (2013.01); *B01J 23/462* (2013.01); *B01J 35/0006* (2013.01)

(58) Field of Classification Search
None
See application file for complete search history.

(56) References Cited

U.S. PATENT DOCUMENTS

| | | |
|---|---|---|
| 8,017,808 B2 | 9/2011 | Eberhardt et al. |
| 8,835,691 B2 | 9/2014 | Klasovsky et al. |
| 8,927,773 B2 | 1/2015 | Klasovsky et al. |
| 8,946,463 B2 | 2/2015 | Klasovsky et al. |
| 2013/0165672 A1* | 6/2013 | Klasovsky ............ C07C 209/16 549/464 |

FOREIGN PATENT DOCUMENTS

| | | |
|---|---|---|
| DE | 102011004465 | 3/2012 |
| DE | 102011075162 | 6/2012 |
| EP | 0312253 | 4/1989 |
| WO | 2007107477 | 9/2007 |
| WO | 2012113475 | 8/2012 |

OTHER PUBLICATIONS

International Search Report for PCT/EP2014/065556, English Translation attached to original, both completed by the European Patent Office on Sep. 26, 2014, All together 7 Pages.
Imm et al. Angew. Chem. Int. Ed. 2011, vol. 50, pp. 7599-7603, "Improved Ruthenium-Catalyzed Amination of Alcohols with Ammonia: Synthesis of Diamines and Amino Esters".
Pingen et al. ChemCatChem 2013, vol. 5, pp. 2905-2912, "Direct Amination of Bio-Alcohols Using Ammonia".

* cited by examiner

*Primary Examiner* — Timothy R Rozof
(74) *Attorney, Agent, or Firm* — Brooks Kushman P.C.

(57) ABSTRACT

A method for synthesizing a primary amine, having the steps of: a) providing at least one dianhydrohexitol, and b) aminating the dianhydrohexitol by reacting same with ammonia, the amination being performed by heterogeneous catalysis using a hydrogenation catalyst in the presence of hydrogen.

17 Claims, 1 Drawing Sheet

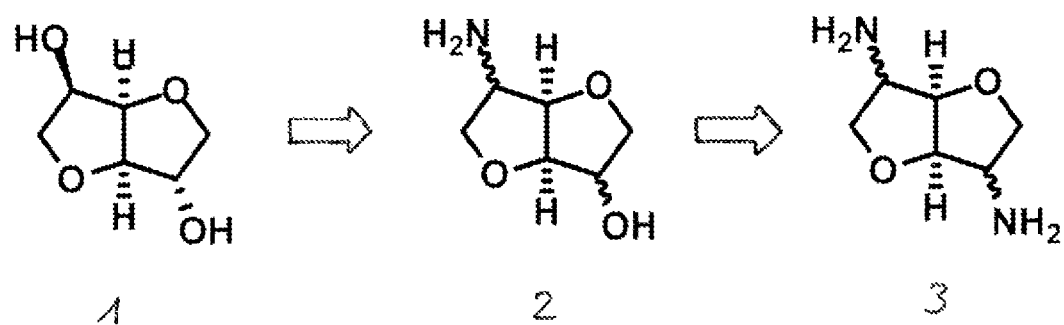

METHOD FOR THE SYNTHESIS OF PRIMARY ISOHEXIDE AMINES

CROSS-REFERENCE TO RELATED APPLICATION

This application is the U.S. national phase of PCT Application No. PCT/EP2014/065556 filed on Jul. 18, 2014, the disclosures of which is incorporated in its entirety by reference herein.

The invention relates to a method for aminating secondary isohexide alcohols to give primary amines.

Biogenic, i.e. preparable from renewable raw materials, platform chemicals have a high economic significance, and a further significant growth in the future of the proportion of plastics from renewable raw materials is envisaged. Among the most important biogenic platform chemicals, sorbitol is attributed a significant role. Sorbitol is produced as a bulk chemical, primarily from sugar- and starch-containing plants. By means of double dehydration of sorbitol, i.e. cleavage of water, isosorbide may be obtained, a sugar alcohol with great potential as a biogenic platform chemical. In addition to obtaining isosorbide from conventionally produced sorbitol, preparation from cellulose directly in a one-stage reaction is also possible. Isosorbide is the most accessible of three isohexides. Isomannide can be produced, in an analogous manner to isosorbide, starting from fructose via mannitol. Isoidide, whose precursor compound occurs only in negligibly small amounts in nature, can be obtained from isosorbide or isomannide by a one-stage isomerization reaction.

Isosorbide, isomannide and isoidide and various bifunctional derivatives thereof have a high potential for applications, for example in biogenic polymers, solvents, fuel additives and also in numerous other fields. In addition to using biogenic diols in polymers, the use of multifunctional amines, which can be prepared from biogenic alcohols, is increasingly of interest, particularly the use of biogenic amines for the production of nitrogen-containing plastics such as polyamides and polyurethanes. The isohexides in particular, bifunctional sugar alcohols, show desirable properties as biogenic monomers in the corresponding polymers.

The preparation of isohexide amines based on dianhydrohexitols is known in principle. However, no synthetic method is known to date for their amination which is efficient enough for industrial production of isohexide amines, for example for the field of novel biomass-based plastics. Either non-catalyzed multi-stage syntheses using some highly reactive or some toxic intermediates are required or laboratory-scale synthetic routes are used which, due to the formation of stoichiometric amounts of by-products, are not considered suitable for scale-up. Therefore, a direct catalytic conversion of the dianhydrohexitols to their amine derivatives is preferable.

Furthermore, although homogeneous catalyzed amination of dianhydrohexitols is known, these are based on molecular catalysts based on expensive noble metal complexes using sophisticated additional ligands which are also only available in minimal amounts, for example molecular ruthenium complexes with various phosphine ligands or pincer complexes. However, the homogeneously catalyzed reactions have distinct disadvantages. These complexes have to be laboriously synthesized and are therefore expensive to prepare. They are usually sensitive to air and water, which complicates their use in catalysis since they must be operated mostly under inert gas atmosphere and in anhydrous organic solvents. Furthermore, the removal of the catalyst from the product is complex and energy-intensive. Overall, these reaction conditions are unsuitable for scaling up and the production of industrial amounts of isohexide amines.

There is a need, therefore, for alternative synthetic methods for isohexide amines. The present invention therefore had the object of providing a method which overcomes at least one of the aforementioned disadvantages of the prior art. In particular, it was the object of the present invention to provide a method which can be used for the industrial production of biogenic isohexide amines.

This object was achieved by a method for preparing a primary amine, comprising the steps of:

a) providing at least one dianhydrohexitol, and
b) amination of the dianhydrohexitol by reaction with ammonia, wherein the amination is carried out by heterogeneous catalysis using a hydrogenation catalyst in the presence of hydrogen.

It has been found, surprisingly, that the method according to the invention allows the conversion of isohexides to primary amines and aminoalcohols using solid catalysts in aqueous solutions and under mild reaction conditions. Suitable solid catalysts are commercially available and enables the reaction under comparatively mild reaction conditions in aqueous solution and also in solvent-free systems in the substrate melt. The solid catalysts can be removed after the reaction by simple filtration and the reaction mixture can be further processed. Thus, a one-step and economic method is provided which can be carried out heterogeneously catalyzed in a particularly advantageous manner in aqueous medium or solvent-free and proceeds selectively with respect to the amines.

By using a commercially available heterogeneous catalyst, Ru/C, mild reaction conditions of 170° C. and 10 bar hydrogen could be provided. These parameters allow for the first time the scale-up of the amination of isohexides to an industrial scale and also, with the good availability of the amine monomers linked thereto, a further development and commercialization of products, particularly plastics, based on biogenic amines. The resulting amines have large market potential, particularly in the production of novel plastics in the range of polyamides and polyurethanes, and also in other market segments of chemical end products such as plasticizers, detergents, pharmaceuticals and agrochemicals.

The term "amination" is understood to mean a reaction in which one or more amine groups are introduced into a molecule. Ammonia can be used as amination reagent. The term "heterogeneous catalysis" is understood to mean catalysis in which catalyst and reacting compounds are present in different phases. The term "hydrogenation catalyst" is understood to mean a catalyst which catalyzes hydrogenation. In the method according to the invention, the heterogeneous hydrogenation catalyst is present as a solid, while the substrate dianhydrohexitol is present in solution or a solvent-free melt and the reaction partner ammonia and hydrogen are present in gaseous and/or in dissolved form.

The dianhydrohexitol provided in step a) is preferably selected from the group comprising isosorbide, isomannide, isoidide and/or mixtures thereof. Dianhydrohexitols, also known as "isohexides", can be synthesized by known methods as described above or are commercially available.

The dianhydrohexitols referred to as "isohexides" are heterocyclic compounds which may be obtained by double dehydration of hexitols such as sorbitol. Isosorbide consists of two V-shaped edge-linked tetrahydrofuran rings having two free hydroxyl groups. The 2-O hydroxyl group is in the exo configuration whereras the 5-O hydroxyl group has the endo configuration. Owing to the different configuration, the two groups have different reactivity and an unequally sterically hindered accessibility. For instance, the 5-O endo hydroxyl group forms an intramolecular hydrogen bond to the opposing ether oxygen atom which increases the nucleophilicity of the OH group. In contrast, the 2-O exo hydroxyl group is sterically unhindered and tends to the formation of intermolecular hydrogen bonds. Two isomers exist in addition to isosorbide: isomannide, in which both hydroxyl groups are in the endo configuration, and isoidide, in which both hydroxyl groups have the exo configuration, which are characterized by a higher symmetry since both hydroxyl groups are present in the same configuration in each case. In the context of the present invention, the terms "dianhydrohexitol" and "isohexide" are used synonymously. Isosorbide is also referred to as 1,4:3,6-dianhydrosorbitol or 1,4:3,6-dianhydroglucitol, isomannide as 1,4:3,6-dianhydromannitol and isoidide as 1,4:3,6-dianhydroiditol. The IUPAC name for isosorbide is (3R, 3aR, 6S, 6aR)-hexahydrofuro[3,2-b]furan-3,6-diol, for isoidide (3S, 3aR, 6S, 6aR)-hexahydrofuro[3,2-b]furan-3,6-diol and for isomannide (3R, 3aR, 6R, 6aR)-hexahydrofuro[3,2-b]furan-3,6-diol.

The method according to the invention provides a heterogeneously catalyzed method for the amination of isohexides or dianhydrohexitols to give diamino-dianhydro-dideoxyhexitols and monoamino-dianhydro-monodeoxyhexitols. Preference is given to heterogeneous hydrogenation catalysts based on metals selected from ruthenium, platinum, palladium and nickel. These may be applied to a support, particularly carbon-containing supports such as carbon, activated carbon or carbon black, or oxides such as aluminum oxide $Al_2O_3$. Hydrogenation catalysts can also be used unsupported, for example in the form of nanoparticles or porous metals such as Raney nickel. The catalysts may also be present in the form of doped or alloyed metals of several elements.

The hydrogenation catalyst used is preferably a supported or unsupported metal catalyst of one or more hydrogenation-active transition metals or noble metals selected from the group comprising platinum, palladium, ruthenium, iridium, rhodium, chromium, molybdenum, tungsten, vanadium, nickel, cobalt, copper and/or iron. Here, the use of two or more transition or noble metals includes particularly hydrogenation-active compounds such as copper chromite and zinc chromite. In preferred embodiments, the hydrogenation catalyst used is a supported or unsupported metal catalyst of a metal selected from the group comprising ruthenium, platinum, palladium and/or nickel. Supported ruthenium, platinum and palladium catalysts are commercially available, for example Ru/C, Ru/$Al_2O_3$, Pd/C, Pt/C, and also Raney nickel. In an advantageous manner, the metals showed good catalytic activity for the amination reaction of the isohexides. Platinum and ruthenium in particular showed good activity. Ruthenium supported on carbon, usually referred to as Ru/C catalyst, is particularly usable. It could be established that in reactions which were catalyzed by Ru/C, about 50% amine derivatives are formed in an advantageous manner. Ruthenium on $Al_2O_3$ as support material is also preferably usable. Ru/$Al_2O_3$ likewise showed good activity in the reaction investigated. Raney nickel also showed good yields particularly at elevated temperatures. In contrast, it has been established that without catalyst only a negligible amount of the isomers of the isohexide reactant of less than one half percent was formed in each case. The loading of the supported catalysts may be varied and are, for example, ca. 5% by weight. In particular, good results were achieved using amounts of 2 mol % Ru/C, Ru/$Al_2O_3$, Pd/C or Pt/C as catalytically active metal species with respect to the amount of substance of the respective substrate. For Raney nickel, good results were achieved using 20 mol %.

Step b) is preferably carried out under positive pressure with reference to atmospheric pressure. For example, the method may be carried out in a reactor such as an autoclave. In an autoclave, the hydrogen may be pressurized to a suitable pressure. In preferred embodiments, the hydrogen is pressurized in a reactor to a hydrogen pressure in the range from ≥1 bar to ≤25 bar, preferably in the range from ≥5 bar to ≤25 bar, preferably in the range from ≥10 bar to ≤25 bar. Here, the pressure values correspond in each case to the pressure pressurized at room temperature corresponding to 20±2° C. In an advantageous manner, 5 bar hydrogen pressure are already sufficient for significant amounts of the monoamines to be formed. A similarly preferable hydrogen pressure is in the range from ≥5 bar to ≤15 bar, preferably in the range from ≥10 bar to ≤15 bar. It has been found that the product composition with respect to the amines was fairly constant in a range from 10 to 25 bar. It is assumed that isomerization reactions may be exploited at higher hydrogen pressures. It has been found, in contrast, that the amination reaction did not proceed without hydrogen under the conditions used.

A major advantage is that exclusion of water and operation under protective gas can be omitted whereby the complexity of the synthesis is significantly reduced and the condition are significantly simplified. The solid catalysts can be readily removed after the reaction, by simple filtration for example, and the reaction mixture further processed. In an advantageous manner, a simpler and more viable route on an industrial scale can be provided to give the isohexide amines in good yield and selectivity.

In preferred embodiments, the amination is carried out at a temperature in the range from ≥100° C. to ≤250° C., preferably in the range from ≥120° C. to ≤230° C., preferably at a temperature in the range from ≥150° C. to ≤200° C. The amination proceeds in good yield even at temperatures in the range from ≥100° C. to ≤150° C., but an increase in the temperature can lead to a more rapid reaction course and also in particular to a larger proportion of amine products. In particular, a temperature in the range from ≥150° C. to ≤200° C., for example 170° C., can lead to a proportion of amine derivatives in the product solution of over 80%. The reaction at a temperature in the range from ≥150° C. to ≤200° C. also requires only a few hours. From a temperature of 250° C., the proportion of by-products may increase.

It has been established that, besides the hydrogen pressure used and the ratio of isohexide to ammonia, the temperature factor showed the most influence on the amination reaction of the isohexides. Other parameters which have been investigated were the reaction time and the stirring speed used. Reaction times in the range from ≥24 h to ≤48 h have proven to be advantageous, particularly with respect to the efficiency and cost-effectiveness of the reaction. It has been established that a doubling of the reaction time from 24 h to 48 h led to a larger proportion of amine products. Furthermore, stirring speeds in the range from ≥500 rpm to ≤1000 rpm have proven to be advantageous. It has been established that a more rapid stirring speed had no influence on the product distribution.

It is particularly advantageous for the industrial production of biogenic amines that the method according to the invention can be carried out in aqueous medium or solvent-free in the substrate melt. Preferably, water is usable as solvent. This can give the advantage that processing or costly disposal of organic solvent is omitted. However, organic solvent may also be suitable, tert-amyl alcohol for example. It is a major advantage, however, that organic solvent can be dispensed with. It has also been established that the use of an organic solvent had no influence on the product distribution.

In preferred embodiments, the amination is carried out in aqueous solution or solvent-free. In particular, it was able to be shown that amination of the isohexides is also possible in the absence of solvent. The amination can be carried out solvent-free in a melt of the dianhydrohexitol. The isohexides melt at a temperature in the range of 60° C. to 70° C. and are therefore present as melts at the preferred reaction temperatures. Ammonia can be introduced in liquid form to a melt of the reactant for example.

Carrying out the amination in aqueous solution or solvent-free allows various possibilities for providing the isohexide and the addition of ammonia. In preferred embodiments, the dianhydrohexitol in step a) is initially charged in solid form or in aqueous solution. In further preferred embodiments, ammonia is added in the form of a gas or liquid or as an aqueous ammonium solution. In an advantageous manner, combinations thereof are possible. Ammonia can be introduced into an autoclave in the form of a gas or liquid, for example with the aid of a metering pump.

By way of example, the dianhydrohexitol may be initially charged in solid form and ammonia may be added in the form of a gas or liquid. Equally preferably, an aqueous ammonia solution can be used. The isohexide may be dissolved in the latter. Particular preference is given to carrying out the amination of the isohexide in aqueous ammonia solution since the latter may serve not only as the ammonia source but also as solvent. The isohexide may also be dissolved in water and the ammonia may be added in the form of a gas or liquid or also in the form of an aqueous solution. For example, water may be used as solvent for the isohexide and ammonia may be added in the form of a gas or liquid. It has been shown that experiments which were carried out in water and ammonia was added separately have only small differences in the product distribution compared to experiments in which the isohexide was initially charged in an aqueous ammonia solution.

Usable aqueous ammonia solutions can have variable concentrations of ammonia, for example in the range from ≥10% by weight to ≤50% by weight, preferably in the range from ≥20% by weight to ≤30% by weight ammonia, based on the total weight of the solution. A 25% (m/m) solution has proven to be especially advantageous.

It is also possible to use ammonium salts, which release ammonia by decomposition under the reaction conditions according to the invention, in a solvent. Preference is given to ammonium salts such as ammonium carbonate, ammonium sulfate, ammonium chloride or ammonium nitrate.

Ammonia may be used in stoichiometric amounts or in excess, based on the hydroxyl groups of the dianhydrohexitol. Ammonia may be present in the range from ≥2 equivalents (eq.) to ≤20 equivalents (eq.), based on the isohexide. In preferred embodiments, ammonia in step b) is present in the range from ≥5 eq. to ≤20 eq., preferably in the range from ≥10 eq. to ≤16 eq., preferably in the range from ≥11 eq. to ≤13 eq., based on the isohexide. At an excess of greater than four equivalents, better yields of amine derivatives, especially diamines, could be achieved. At a larger excess of ammonia, 27 equivalents for example, the product distribution was not influenced towards a greater yield of amines. Good results can be obtained, particularly in the range from ≥10 eq. to ≤16 eq., preferably in the range from ≥11 eq. to ≤13 eq., based on the isohexide. 11 equivalents (eq.) of ammonia with respect to the isosorbide correspond in this case to about 5 equivalents based on one hydroxyl group.

It is assumed that the preparation of isohexide amines proceeds in two reaction steps in which firstly an aminoalcohol, also called monoamine, is formed, which can subsequently further react to the diamine. It is further assumed that the catalytic amination of dianhydrohexitols proceeds in three steps in which, after a metal-catalyzed dehydration of the alcohol to the ketone, imine formation takes place, which proceeds uncatalyzed, and subsequently the imine is hydrogenated catalytically to give the diamine product. The imine forms a prochiral center. Therefore, both possible configurations of the amine function (endo/exo) can be formed, independently of which configuration the corresponding hydroxyl group previously had. For this reason and the fact that both disubstituted and monosubstituted amine derivatives can be formed, the product spectrum can include four aminoalcohols, also called monoamines, and three diamines with various stereochemistries. In addition, the ketone as intermediate has a prochiral center and can also be further hydrogenated such that, independently of the starting material, all three isohexide isomers can be formed.

At a low excess of ammonia of 4 eq., a yield exclusively of monoamines could be established, whereas at an excess of 11 eq., better yields of amine derivatives, especially diamines, were established.

Furthermore, the product distribution can be influenced depending on the substrate by selection of the isohexide reactant. The dianhydrohexitol provided in step a) is preferably selected from the group comprising isosorbide, isomannide, isoidide and/or mixtures thereof. It was able to be established that, starting from isomannide as starting material, somewhat more amine derivatives were formed than when using isosorbide. Furthermore, a significantly greater amount of diamines was formed starting from isomannide.

Overall, a method can be provided which allows amination of the isohexides using commercially available heterogeneous catalysts and industrially scalable conditions. Ru/C is particularly preferred and preferred mild reaction conditions are 170° C. and 10 bar hydrogen pressure. Furthermore, a procedure in aqueous ammonia solution and an excess of 11 eq. based on the isohexide have proven to be especially advantageous. In this case, the reaction can be conducted within 24 hours with a good yield. These parameters allow for the first time the scale-up of this reaction to the industrial scale and, with the associated good availability of the amine monomers, further development and commercialization of the products.

Examples and figures which serve to illustrate the present invention are specified below.

Here shown:

FIG. 1 the preparation of isohexide amines in two reaction steps with isosorbide as example FIG. 1 shows that, by reacting isosorbide or 1,4:3,6-dianhydrosorbitol 1 with $NH_3$, initially the aminoalcohol 2, also called monoamine, is formed, which subsequently further reacts also by reaction with $NH_3$ to give the diamine 3.

The amination of isosorbide 1 according to the invention takes place by means of heterogeneous catalysis using a hydrogenation catalyst in the presence of hydrogen.

General Procedure for the Amination:

The experiments were carried out in a 45 mL autoclave. The experiments in 5 mL of organic solvent or water were carried out with 1 g (6.8 mmol) of isohexide and 2 mol % catalyst (0.137 mmol of metal species) with respect to the catalytically active metal species. The experiments with Raney nickel were an exception in which 20 mol % was used. In the experiments without solvent, 5 g of isohexide (34.2 mmol) were used and the amount of catalyst correspondingly adjusted. The ammonia was either pure and introduced into the autoclave in liquid form with the aid of a metering pump or a 25% (m/m) aqueous ammonia solution was used which served simultaneously as solvent.

In each experiment, after pressurizing the hydrogen, where the pressure value corresponded in each case to the pressurized pressure at room temperature (20±2° C.), the autoclave was heated to the appropriate temperature and the reaction stopped after 24 to 48 h inclusive of the heating phase. The catalyst was filtered off from the reaction solution and the samples were investigated after derivatization by gas chromatography (GC).

Gas Chromatography:

The product solutions were analyzed by gas chromatography. For this purpose, the samples were firstly derivatized using chlorotrimethylsilane. The individual products were separated by means of gas chromatography. The monoamines and diamines were further differentiated with the aid of gas chromatography coupled with mass spectrometry (GC-MS). For the evaluation, the areas of the individual components were determined and normalized to 100%.

Example 1

Amination of Isosorbide Using Different Catalysts

The experiments for the amination of isosorbide using different catalysts were carried out as described in the general procedures where 5 mL of a 25% (m/m) aqueous ammonia solution were used. The latter served as ammonia source and solvent for 1 g of isosorbide (6.8 mmol, Alfa Aesar, 98%). The 5 mL of 25% solution used corresponded to 11 equivalents (eq.) of ammonia with respect to the isosorbide or 5 based on one hydroxyl group. In each case, 277 mg of Ru/C (Sigma-Aldrich), 277 mg of Ru/Al$_2$O$_3$, 292 mg of Pd/C, 535 mg of Pt/C and 180 mg of a slurry of Raney nickel were added. This corresponded in each case to 2 mol % catalyst (0.137 mmol) with respect to the catalytically active metal species of the supported catalysts. The loading of the supported catalysts was 5% by weight in each case. In experiments with Raney nickel, 20 mol % was used. Blank experiments without catalyst were carried out as controls. The experiments were carried out at a temperature of 170° C., 11 eq. of NH$_3$, 10 bar hydrogen pressure, 500 rpm stirring speed and 24 hours reaction time.

It was shown that platinum and ruthenium show moderate to good activity. In the reaction catalyzed by Ru/C, about 50% amine derivatives were formed. For platinum and ruthenium respectively, 1% or 1% of a mixture of the diamines diaminoisorsorbide, diaminoisomannide and diaminoisoidide were obtained and 18% or 49% of the four monoamines. Pd/C showed a somewhat lower activity in the amination reaction and the activity of Raney nickel was also lower in comparison. Raney nickel mainly catalyzed the isomerization of the sugar alcohol. In the comparative experiment without catalyst, only a negligible amount of the isomers of isosorbide of less than one half percent was obtained in each case.

Example 2

Amination of Isosorbide with Variation of the Hydrogen Pressure

To investigate the influence of the hydrogen pressure, experiments were carried out at 5 bar, 10 bar, 15 bar and 25 bar and also without hydrogen. The experiments were carried out as described in the general experimental procedure in which 5 mL of a 25% (m/m) aqueous ammonia solution were used as ammonia source and solvent for 1 g of isosorbide (6.8 mmol). Here, 2 mol % Ru/C as catalyst (0.137 mmol) were used with respect to the catalytically active metal species. The experiments were carried out with Ru/C as catalyst, 11 eq. of NH$_3$, at a temperature of 170° C., 500 rpm stirring speed, 24 hours reaction time and a hydrogen pressure in each case of 5 bar, 10 bar, 15 bar or 25 bar and also without hydrogen.

It showed that the reaction did not proceed under the conditions used without hydrogen. A hydrogen pressure of 5 bar proved to be already sufficient such that significant amounts of 44% of the monoamines were formed. No significant differences in the product composition with respect to the amines could be observed between the results of the experiments at 10, 15 and 25 bar. 50%, 49% or 47% of a mixture of the monoamines were obtained respectively, and also <3% of a mixture of the diamines in each case.

It was further shown that with increasing pressure greater amounts of isoidide were formed. It is assumed that the isomerization reaction to give isoidide is exploited at higher hydrogen pressures.

Example 3

Amination of Isosorbide with Variation of Various Parameters

The experiments were carried out as described in the general experimental procedure. An experimental approach using 5 mL of a 25% (m/m) aqueous ammonia solution corresponding to 11 eq. of NH$_3$, 1 g of isosorbide (6.8 mmol), 2 mol % Ru/C as catalyst (0.137 mmol), a temperature of 170° C., 500 rpm stirring speed, 24 hours reaction time and a hydrogen pressure of 10 bar was set as standard. Deviations therefrom in five experiments in which one parameter was changed in each case, wherein a temperature of 200° C., a reaction time of 48 hours, a stirring speed of 1000 rpm, the use of 2 mol % Ru/Al$_2$O$_3$ as catalyst and 16 equivalents of NH$_3$, were investigated.

It was shown that a somewhat larger excess of 16 eq. of ammonia and a more rapid stirring speed had no influence on the product distribution. A doubling of the reaction time leads to a greater proportion of amine products, likewise an increase in temperature. The latter even leads to a proportion of amine derivatives in the product solution of over 80%. 79% of monoamines and 3.4% of diamines were obtained. It was further shown that Al$_2$O$_3$ as support material for ruthenium also showed good results and therefore Ru/Al$_2$O$_3$ likewise showed good activity in the reaction investigated.

Example 4

Amination of Isomannide

The amination of isomannide was carried out as described in the general experimental procedure in which 1 g of isomannide (6.8 mmol, Sigma Aldrich, 95%) as reactant in 5 mL of 25% (m/m) aqueous ammonia solution corresponding to 11 eq. of NH$_3$ and using 2 mol % Ru/C as catalyst (0.137 mmol), at a temperature of 170° C., 500 rpm stirring speed, 24 hours reaction time and a hydrogen pressure of 10 bar was set. For the comparison, 1 g of isosorbide was reacted as reactant under otherwise identical conditions.

Starting from isomannide as starting material, somewhat more amine derivatives were formed compared to isosorbide, 59% in comparison to 50%. In addition, two other monoamines were preferably formed. Starting from isomannide, significantly more diamines were obtained, with a proportion of 16% of the product mixture, than the <1% obtained when using isosorbide.

It was further established that, starting from isomannide, the monoamines were formed having a stereochemistry which are not formed in the reaction starting from isosorbide. It is assumed that this may be due to the different configuration or reactivity of the hydroxyl groups. The hydroxyl group with endo configuration seems to be preferably dehydrated and accordingly also aminated. Since in isomannide both hydroxyl groups have an endo configuration, the remaining hydroxyl group in both aminoalcohols should also have an endo configuration. In isosorbide there is both an endo- and exo-configured hydroxyl group and, for the reasons mentioned, the remaining hydroxyl group in the aminoalcohols from isosorbide should accordingly have an exo configuration. Therefore, it is assumed that, starting from isomannide, a significantly greater amount of diamines is formed.

Example 5

Amination of Isomannide with Variation of Various Parameters

The experiments were carried out as described in the general experimental procedure. An experimental approach using 5 mL of 25% (m/m) aqueous ammonia solution corresponding to 11 eq. of $NH_3$, 1 g of isomannide (6.8 mmol), 2 mol % Ru/C as catalyst (0.137 mmol), a temperature of 170° C., 500 rpm stirring speed, 24 hours reaction time and a hydrogen pressure of 10 bar was set as standard. One parameter was changed in each of six experiments by deviations therefrom. Firstly, in two batches a temperature of 200° C. and a reaction time of 48 hours were investigated.

Furthermore, experiments were carried out in water or tert-amyl alcohol as solvent and also solvent-free. For this, pure liquid ammonia was metered into the autoclave. Two batches of 1 g of isomannide in 5 mL of water were initially charged and ammonia in liquid form at the ratio of 13 or 27 equivalents was introduced into the autoclave with the aid of a metering pump. In a further batch, 1 g of isomannide in 5 mL of tert-amyl alcohol was initially charged and ammonia in liquid form was introduced into the autoclave at the ratio of 13 equivalents. In one batch without solvent, 5 g of isomannide (34.2 mmol) were used and the amount of catalyst correspondingly adjusted. The ammonia also in liquid form at the ratio of 4 equivalents was introduced into the autoclave with the aid of a metering pump.

It was established that the proportions of amine derivatives increased also when using isomannide as reactant with a longer reaction time and a higher temperature. Thus, in the batch at a temperature of 170° C. and 24 hours reaction time, 59% of amine derivatives were obtained, whereas at 200° C., 90% and at a reaction time of 48 hours, 71% were obtained. As in the reactions with isosorbide, the temperature factor showed the greatest influence.

The experiments in which water was used as solvent and ammonia was added separately had only minor differences compared to the use of aqueous ammonia solution. At a similar ammonia excess of 11 to 13 eq in the latter, the proportions of amine derivatives were somewhat lower. It was also established that two of the monoamines were not formed. Also a greater excess of ammonia of 27 eq. compared to 11 eq. had no notable influence on the product distribution. It was also shown that a switch to an organic solvent, tert-amyl alcohol had no notable influence on the product distribution.

Furthermore, the amination of isomannide without solvent likewise showed formation of amine derivatives. This shows that the solvent-free amination of isomannide is also possible. Here, only a small excess of ammonia, which in this experiment at about 4 eq. was significantly below the 11 eq. used as comparison, resulted in a lower yield of amine derivatives, which were exclusively monoamines.

Overall, the examples show that the conversion of the biogenic alcohols isosorbide and isomannide to their amine derivatives could be achieved by means of heterogeneous catalysis using a hydrogenation catalyst in the presence of hydrogen in aqueous solution and even solvent-free. Using a commercially available heterogeneous catalyst, Ru/C, mild reaction conditions of 170° C. and 10 bar hydrogen could be achieved, which allows for the first time the scaling-up of this reaction to the industrial scale.

The invention claimed is:

1. A method for preparing a primary amine comprising the steps of:
    a) providing at least one dianhydrohexitol, and
    b) amination of the dianhydrohexitol by reaction with ammonia,
    wherein the amination is carried out by heterogeneous catalysis using a hydrogenation catalyst in the presence of hydrogen.
2. The method as claimed in claim 1, wherein the hydrogenation catalyst used is a supported or unsupported metal catalyst of one or more hydrogenation-active transition metals or noble metals selected from the group comprising platinum, palladium, ruthenium, iridium, rhodium, chromium, molybdenum, tungsten, vanadium, nickel, cobalt, copper and iron.
3. The method as claimed in claim 1, wherein the hydrogen is pressurized in a reactor to a hydrogen pressure in the range from ≥1 bar to ≤25 bar.
4. The method as claimed in claim 1, wherein the amination is carried out at a temperature in the range from ≥100° C. to ≤250° C.
5. The method as claimed in claim 1, wherein the amination is carried out in aqueous solution or solvent-free.
6. The method as claimed in claim 1, wherein the dianhydrohexitol in step a) is initially charged in solid form or in aqueous solution.
7. The method as claimed in claim 1, wherein ammonia is added in the form of a gas or liquid or as an aqueous ammonium solution.
8. The method as claimed in claim 1, wherein the ammonia in step b) is present in the range from ≥5 eq. to ≤20 eq., based on the dianhydrohexitol.
9. The method as claimed in claim 1, wherein the dianhydrohexitol provided in step a) is selected from the group comprising isosorbide, isomannide, isoidide and/or mixtures thereof.
10. The method as claimed in claim 1, wherein the hydrogenation catalyst used is a supported or unsupported metal catalyst of one or more hydrogenation-active transition metals or noble metals selected from the group comprising ruthenium, platinum, palladium and nickel.
11. The method as claimed in claim 1, wherein the hydrogenation catalyst is ruthenium supported on carbon.

12. The method as claimed in claim 1, wherein the hydrogen is pressurized in a reactor to a hydrogen pressure in the range from ≥5 bar to ≤25 bar.

13. The method as claimed in claim 1, wherein the hydrogen is pressurized in a reactor to a hydrogen pressure in the range from ≥10 bar to ≤25 bar.

14. The method as claimed in claim 1, wherein the amination is carried out at a temperature in the range from ≥120° C. to ≤230° C.

15. The method as claimed in claim 1, wherein the amination is carried out at a temperature in the range from ≥150° C. to ≤200° C.

16. The method as claimed in claim 1, wherein the ammonia in step b) is present in the range from ≥10 eq. to ≤16 eq., based on the dianhydrohexitol.

17. The method as claimed in claim 1, wherein the ammonia in step b) is present in the range ≥11 eq. to ≤13 eq., based on the dianhydrohexitol.

\* \* \* \* \*